Figure 1:
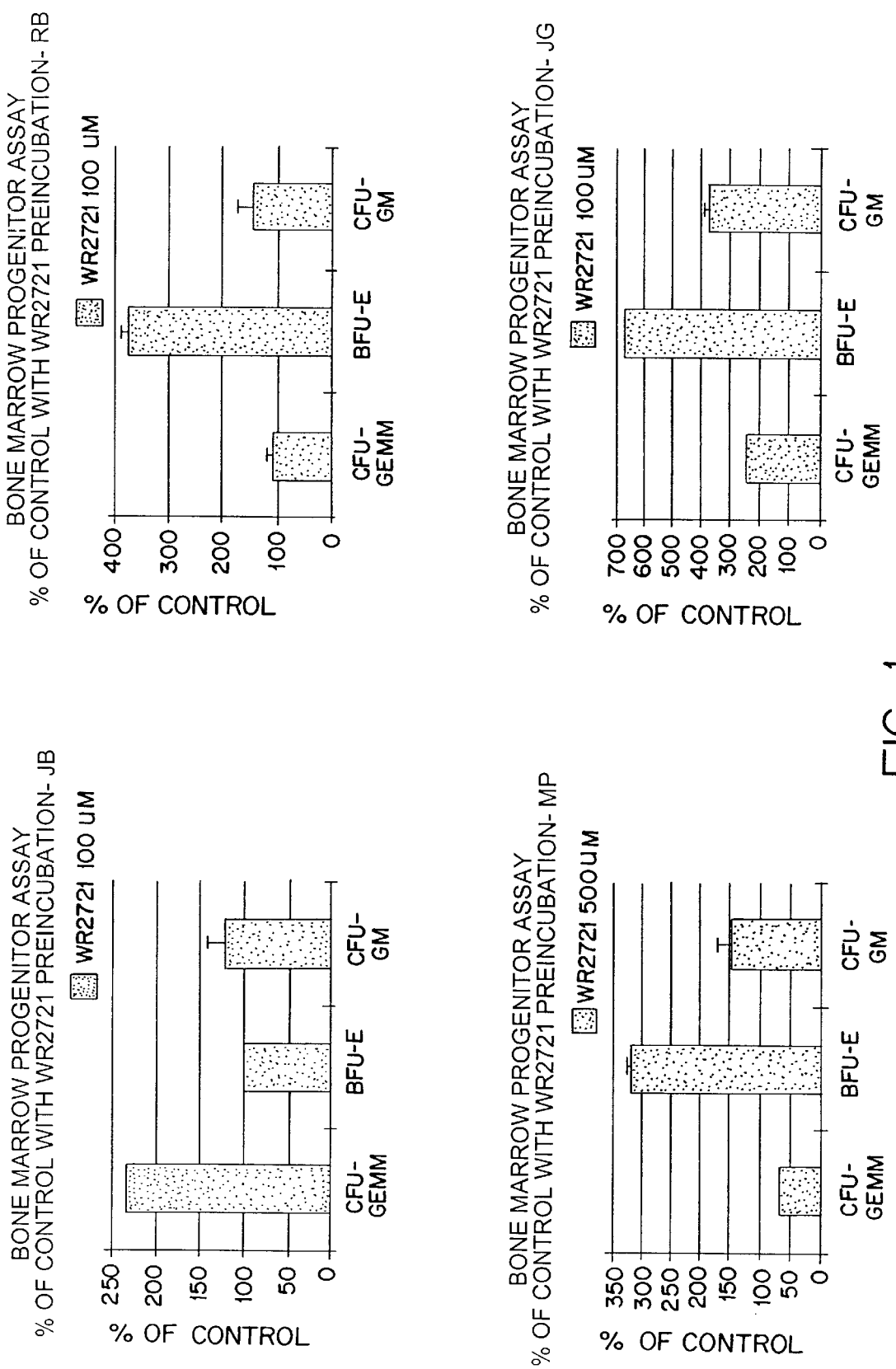

United States Patent [19]
Capizzi et al.

[11] Patent Number: 5,906,984
[45] Date of Patent: *May 25, 1999

[54] METHODS OF USING AMINOTHIOLS TO PROMOTE HEMATOPOIETIC PROGENITOR CELL GROWTH

[75] Inventors: Robert L. Capizzi, Haverford, Pa.; Alan F. List, Tucson, Ariz.

[73] Assignees: Arizona Board of Regents on behalf of The University of Arizona, Tucson, Ariz.; U.S. Bioscience, West Conshohocken, Pa.

[*] Notice: This patent is subject to a terminal disclaimer.

[21] Appl. No.: 09/046,870

[22] Filed: Mar. 24, 1998

Related U.S. Application Data

[63] Continuation of application No. 08/390,713, Feb. 17, 1995, Pat. No. 5,846,958.

[51] Int. Cl.[6] ........................... A61K 31/66; A61K 31/13
[52] U.S. Cl. ............................... 514/114; 514/665
[58] Field of Search ..................... 514/114, 665

[56] References Cited

U.S. PATENT DOCUMENTS 3,892,824  7/1975  Piper et al. ..................... 260/944

OTHER PUBLICATIONS

Toohey, Proc. Nat. Acad Sci, USA. vol. 72 (1) pp. 73–77, Jan. 1975.
CA 110 : 7195,X, 1989.
Patchen et al, Seminars in Oncology, vol. 21 (5) Suppl. 11, 26–32, 1994.
Ash et al., "Studies of Human Pluripotential Hemopoietic Stem Cells (CFU–GEMM) In Vitro," *Blood*, 58(2), 309–316 (1981).

Douay et al., "Amifostine (WR–2721) protects normal hematopoietic stem cells against cyclophosphamide derivatives' toxicity without compromising their antileukemic effects," *Chemical Abstracts*, 123:306175 (1995).

Hankins et al., "Effects of Sulfhydryl Compounds on Friend Virus–infected Spleen Cells in Vitro," *J. Biol. Chem.*, 254(13), 5701–5707 (1979).

Helgestad et al., "Vitamin C and Thiol Reagents Promote the In Vitro Growth of Murine Granulocyte/Macrophage Progenitor Cells by Neutralizing Endogenous Inhibitor(s)," *Blut*, 52, 1–8 (1986).

Patchen et al., "Granulocyte Colony–Stimulating Factor and Amifostine (Ethyol) Synergize to Enhance Hemopoietic Reconstitution and Increase Survival in Irradiated Animals," *Seminars in Oncology*, 21(5), Suppl. 11, 26–32 (1994).

Patchen et al., "Postirradiation Glucan Administration Enhances the Radioprotective Effects of WR–2721," *Radiation Research*, 117, 59–69 (1989).

Toohey, "Sulfhydryl Dependence in Primary Explant Hematopoietic Cells. Inhibition of Growth In Vitro with Vitamin $B_{12}$ Compounds," *Proc. Nat. Acad. Sci. USA*, 72(1), 73–77 (1975).

*Primary Examiner*—Rebecca Cook
*Attorney, Agent, or Firm*—Pennie and Edmonds

[57] ABSTRACT

The present invention relates to methods of stimulating he growth of hematopoietic progenitor cells. In particular, it relates to the use of thiols and related compounds in stimulating the growth of hematopoietic progenitor cells in vitro and in vivo. Furthermore, the present invention relates to methods of using these compounds for the treatment of marrow failure states and immunodeficient conditions, including but not limited to myelodysplastic syndromes and acquired immunodeficiency syndrome.

22 Claims, 1 Drawing Sheet

METHODS OF USING AMINOTHIOLS TO PROMOTE HEMATOPOIETIC PROGENITOR CELL GROWTH

This is a continuation of application Ser. No. 08/390,713, filed Feb. 17, 1995, now U.S. Pat. No. 5,846,958 which is incorporated herein in its entirety.

1. INTRODUCTION

The present invention relates to methods of stimulating the growth of hematopoietic progenitor cells. In particular, it relates to the use of thiols and related compounds in stimulating the growth of hematopoietic progenitor cells in vitro and in vivo. Furthermore, the present invention relates to methods of using these compounds for the treatment of marrow failure states and immunodeficient conditions, including but not limited to myelodysplastic syndromes and acquired immunodeficiency syndrome.

2. BACKGROUND OF THE INVENTION

A variety of diseases and disorders, including premalignancy, overt malignancy and immunodeficiency, are related to malfunction within the lympho-hematopoietic system. Some of these conditions could be alleviated and/or cured by repopulating the lympho-hematopoietic system with progenitor cells, which when triggered to differentiate would overcome the patient's deficiency. Therefore, the ability to initiate and regulate hematopoiesis is of great importance (McCune et al., 1988, Science 241:1632).

In humans, a form of successful therapy is bone marrow transplantation. Apart from the use of bone marrow transplantation in the treatment of leukemia, it is now frequently being used in other neoplasia (Epstein and Slease, 1985, Surg. Ann. 17:125). This type of therapy, however, is both painful (for donor and recipient) because of the involvement of invasive procedures and can cause severe and even fatal complications to the recipient, particularly with allogeneic transplant and related Graft Versus Host Disease (GVHD) results. Therefore, the risk of GVHD restricts the use of bone marrow transplantation to patients with otherwise fatal diseases. An alternative approach to therapy for hematopoietic disorders is the use of growth factors or cytokines to stimulate blood cell development in a recipient (Dexter, 1987, J. Cell Sci. 88:1; Moore, 1991, Annu. Rev. Immunol. 9:159).

The process of blood cell formation, by which a small number of self-renewing stem cells give rise to lineage specific progenitor cells that subsequently undergo proliferation and differentiation to produce the mature circulating blood cells has been shown to be at least in part regulated by specific hormones. These hormones are collectively known as hematopoietic growth factors, (Metcalf, 1985, Science 229:16; Dexter, 1987, J. Cell Sci. 88:1; Golde and Gasson, 1988, Scientific American, July:62; Tabbara and Robinson, 1991, Anti-Cancer Res. 11:81; Ogawa, 1989, Environ. Health Presp. 80:199; Dexter, 1989, Br. Med. Bull. 45:337). With the advent of recombinant DNA technology, a number of these molecules have now been cloned and expressed in recombinant form (Souza et al., 1986, Science 232:61; Gough et al., 1984, Nature 309:763; Yokota et al., 1984, Proc. Natl. Acad. Sci. U.S.A. 81:1070; Kawasaki et al., 1985, Science 230:291).

These growth factors have been studied in their structure, biology and even therapeutic potential. Some of the most well characterized factors include erythropoietin (EPO), stem cell factor (SCF), granulocyte macrophage colony stimulating factor (GM-CSF), macrophage colony stimulating factor (M-CSF), granulocyte colony stimulating factor (G-CSF), and the interleukins. These factors act on different cell types at different stages during blood cell development, and their potential uses in medicine include lessening the need for blood transfusions, speeding bone marrow recovery following transplantation and cytotoxic cancer therapy, correcting immunosuppressive disorders, wound healing, and activation of the immune response. (Golde and Gasson, 1988, Scientific American, July:62). Apart from inducing proliferation and differentiation of hematopoietic progenitor cells, such cytokines have also been shown to activate a number of functions of mature blood cells (Stanley et al., 1976, J. Exp. Med. 143:631; Schrader et al., 1981, Proc. Natl. Acad. Sci. U.S.A. 78:323; Moore et al., 1980, J. Immunol. 125:1302; Kurland et al., 1979, Proc. Natl. Acad. Sci. U.S.A. 76:2326; Handman and Burgess, 1979, J. Immunol. 122:1134; Vadas et al., 1983, Blood 61:1232; Vadas et al., 1983, J. Immunol. 130:795), including influencing the migration of mature hematopoietic cells (Weibart et al., 1986, J. Immunol. 137:3584).

Although these growth factors have been shown to possess proliferative and/or differentiative effects on various hematopoietic cell lineages, they have not proven effective in many clinical disease settings. For example, myelodysplastic syndromes (MDS) comprise a diverse group of hematopoietic stem cell disorders characterized by ineffective blood cell production, progressive cytopenias and a variable risk of progression to acute leukemia (List et al., 1990, J. Clin. Oncol. 8:1424). Clinical trials of MDS patients treated with recombinant human granulocyte-macrophage colony-stimulating factor and recombinant human granulocyte-colony stimulating factor have shown that while these cytokines can restore granulocytopoiesis in treated patients, the efficacy is restricted to the granulocyte/monocyte lineage with little or no improvement in hemoglobin and/or platelet counts (Schuster et al., 1990, Blood 76 (Suppl.1):318a). When such patients were recently treated with recombinant human erythropoietin, a sustained improvement in hemoglobin and/or decrease in transfusion requirement was achieved in only less than 25% of patients (Besa et al., 1990, 76 (Suppl.1):133a; Hellstrom et al., 1990, 76 (Suppl.1):279a; Bowen et al., 1991, Br. J. Haematol. 77:419). Thus, there remains a need for an effective agent for the treatment of marrow failure states such as MDS.

Furthermore, cytokines are both difficult and costly to produce. Because these factors are proteins, their production is not amenable to direct chemical synthesis. Moreover, their low endogenous expression levels and the limited growth rate of human cells make the natural production of these proteins extremely costly. Their production by recombinant methods also entails large economic costs and technical obstacles. Hence, none of these previously reported molecules provides both a biologically active and readily synthesized stimulator of hematopoietic progenitor cells for in vivo administration.

3. SUMMARY OF THE INVENTION

The present invention relates to the use of thiols and related compounds in the stimulation of hematopoietic progenitor cells. Such thiol compounds are readily synthesized using the teachings of U.S. Pat. No. 3,892,824. The invention is based, in part, on Applicants' discovery of the previously unknown efficacy of a thiol compound, amifostine, in the stimulation of hematopoietic progenitor cells. The hematopoietic progenitor cells may be stimulated by culturing the cells and treating them with the thiol compounds in vitro. Alternatively, the thiol compounds may be directly administered to a patient who is in need of higher numbers of blood cells. Thus the invention provides methods for treating conditions that require hematopoietic progenitor cell proliferation, including but not limited to marrow failure states such as MDS and immunodeficiency.

4. BRIEF DESCRIPTION OF THE DRAWINGS

FIGS. 1A–1D. Bone marrow colony formation assay. Bone marrow cells isolated from four patients with MDS were treated with amifostine, washed and plated in methylcellulose. Control samples were untreated with this compound. Each sample was then assayed for CFU-GEMM, BFU-E, and CFU-GM colony formation.

5. DETAILED DESCRIPTION OF THE INVENTION

The present invention is based in part on the Applicants' discovery that amifostine stimulates hematopoietic progenitor cells in vitro. On this basis, the present invention encompasses the use of thiols and polyamines and their functional derivatives or analogues in methods of treating any conditions that require hematopoietic cell growth.

5.1. Compounds

The stimulation of hematopoietic progenitor cells in accordance with the invention may be achieved by treatment with thiol compounds that are suitable for human use with minimal toxicity. In particular, the present invention relates to aminothiols having the formula $RNH(C_nH_{2n})NH(C_nH_{2n})SPO_3H_2$ wherein R is hydrogen, an aryl, an acyl, or an alkyl group containing from 1 to 7 carbon atoms and each n has a value of from 2 to 6; or hydrates and pharmaceutically acceptable salts thereof such as halogen salts and/or alkali metal salts. Such compounds and their synthesis are described in detail in Piper and Johnston, U.S. Pat. No. 3,892,824, which is incorporated herein by reference in its entirety. Such compounds include but are not limited to amifostine, glutathione, N-acetyl cysteine, sodium thiosulfate, and the like, and they can be prepared by methods well known to those skilled in the art, see, for example, F. Cortese, "Organic Syntheses", Coll. bol. II, A. H. Blatt, Ed., John Wiley and sons, Inc., New York, N.Y., 1943, pp. 91–93; S. Akerfeldt, Acta Chem Scand., 1960, 14: 1980; and J. R. Piper et al., Chem. Ind. (London), 1966, p. 2010.

The preparation of the preferred compound, S-2-(3-aminopropylamino)ethyl Dihydrogen Phosphorothioate Monohydrate $H_2N(CH_2)_3NHCH_2CH_2SPO_3H_2 \cdot H_2O$ (amifostine or WR 2721) has also been described in detail in Piper and Johnston, U.S. Pat. No. 3,892,824, which is incorporated herein by reference in its entirety. The dephosphorylated form of this compound is its free thiol active metabolite (WR 1065). In addition, a room temperature stable trihydrate form has also been synthesized.

For oral administration, the preferred compound is WR 151327 (chemical nomenclature: 1-propanethiol-3-[[3-(methylamino)propyl]amino]-dihydrogen phosphorothioate) which is depicted as follows:

$CH_3NH\,(CH_2)_3NH(CH_2)_3SPO_3H_2$.

WR 151327 is a thiophosphate reducing agent with oxygen-free radical scavenging capacity (Grdina et al., 1991, supra) which exerts its anti-HIV activity without killing cells or inhibiting their growth. WR 151326 is the dephosphorylated free thiol. Since these compounds are capable of inhibiting HIV activity, they may be particularly useful in treating HIV patients to achieve both anti-HIV and hematopoietic cell stimulatory effects.

5.2. Uses of the Compounds

The compounds of the present invention may be directly administered to patients for the treatment of any conditions that manifest reduced numbers of circulating blood cells including but not limited to anemia, leukopenia, thrombocytopenia individually or as pancytopenia and various forms of immunodeficient states. Alternatively, the compounds may be used to expand the numbers of hematopoietic progenitor cells in culture, and the cells are then infused intravenously into patient. For the in vitro or ex vivo incubation of bone marrow or peripheral blood stem cells with thiols, a preferred dose range is between 0.1 $\mu$M–5 mM. The methods of the invention may be useful to treat any conditions associated with reduced blood cell numbers, including but not limited to, acquired and congenital marrow failure states and immunodeficiency syndromes such as Fanconi anemia, congenital neutropenia and MDS, and cytotoxic cancer therapy.

In vivo administration of the compounds disclosed in Section 5.1. supra may be performed in the following manner. Groups of patients with bone marrow failure may first receive intravenous infusion of graded doses of the compounds at 100 mg/m$^2$, 200 mg/M$^2$, 400 mg/m$^2$ or 740 mg/M$^2$ to determine a maximum tolerated dose. Thereafter, patients may be treated with the pre-determined dose three times per week for three weeks. Following a fourteen-day rest period, the patients may be evaluated for hematologic response by cell count and colony formation. Responsive patients may continue the treatment until peripheral cell counts return to normal levels.

5.3. Pharmaceutical Formulations and Routes of Administration

The identified compounds can be administered to a human patient, by itself, or in pharmaceutical compositions where it is mixed with suitable carriers or excipient(s) at doses to treat or ameliorate a variety of disorders, including but not limited to MDS. A therapeutically effective dose further refers to that amount of the compound sufficient to result in an increase of blood cell count as compared to the pretreatment condition. Techniques for formulation and administration of the compounds of the instant application may be found in "Remington's Pharmaceutical Sciences," Mack Publishing Co., Easton, Pa., latest edition.

5.3.1. Routes of Administration

Suitable routes of administration may, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than systemic manner, for example, via injection of the compound directly into the bone marrow, often in a depot or sustained release formulation.

Furthermore, one may administer the compound in a targeted drug delivery system, for example, in a liposome and/or conjugated with a cell-specific antibody. The liposomes and cell-specific antibody will be targeted to and taken up selectively by the bone marrow cells.

5.3.2. Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compound of the invention may be formulated in appropriate aqueous solutions, such as physiologically compatible buffers such as Hanks's solution, Ringer's solution, or physiological saline buffer. For transmucosal and transcutaneous administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a cosolvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the hematopoietic progenitor cell stimulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

5.3.3. Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the EC50 (effective dose for 50% increase) as determined in cell culture, i.e., the concentration of the test compound which achieves a half-maximal stimulation of marrow progenitor cell replication as assayed by the formation of BFU-E, CFU-GEMM, CFU-GM, etc. Such information can be used to more accurately determine useful doses in humans.

A therapeutically effective dose refers to that amount of the compound that results in amelioration of symptoms related to the increase in blood cell numbers or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch.1, p.1).

Dosage amount and interval may be adjusted individually to provide plasma levels of the active moiety which are sufficient to maintain the progenitor cell stimulatory effects. Usual patient dosages for systemic administration range from 100–2000 mg/day. Stated in terms of patient body surface areas, usual dosages range from 50–910 mg/m$^2$/day. Usual average plasma levels should be maintained within 0.1–1000 $\mu$M.

In cases of local administration or selective uptake, the effective local concentration of the drug may not be related to plasma concentration.

The amount of composition administered will, of course, be dependent on the subject being treated, on the subject's body surface area, the severity of the affliction, the manner of administration and the judgment of the prescribing physician.

5.3.4. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of immunodeficiency.

6. EXAMPLE

Amifostine is a Stimulator or Hematopoietic Progenitor Cells

Previous studies have reported several sulfhydryl compounds to have certain in vitro stimulatory effects on hematopoietic cells (Helgestad, et al., 1986, Blut 52: 1–8; Ash et al., 1981, Blood, 58: 309–316; Toohey, 1975, Proc. Natl. Acad. Sci. USA 72: 73–77; and Hankins and Krantz, 1979, J. Biol. Chem. 254: 5701–5707). These compounds, however, have not been shown to possess growth promoting effect in vivo and in fact, some of these compounds are not suitable for in vivo administration because of their toxicity. In addition, it has also been suggested that these compounds function by neutralizing endogenous inhibitors in growth factor containing conditioned media due to their anti-oxidant activity. In contrast, amifostine is shown herein to stimulate progenitor cell growth. Its cell growth-promoting activity was found to be greater than that of the several recombinant cytokines. Also, unlike glutathione, amifostine was not toxic to marrow progenitor cells even at very high concentrations. Amifostine was originally developed as a cytoprotective agent against ionizing radiation. While it has been shown to protect normal tissues from cytotoxicity of radiation, alkylating agents and platinum analogs, it was not tested as a cell growth-promoting agent prior to the present invention.

6.1. MATERIALS AND METHODS

Bone marrow specimens were obtained by marrow aspirate from normal individuals or patients with MDS. Mononuclear cell fractions were isolated from heparinized marrow samples by Ficoll Hypaque density centrifugation. $2\times10^6$ bone marrow mononuclear cells were incubated with WR1065 (the free thiol active metabolite of amifostine), or amifostine (WR 2721) at various concentrations. The incubation was for 15 minutes and then the cells were pelleted, washed twice in 10 ml of culture medium and plated in methylcellulose for colony formation. For comparison, the cells were also incubated with glutathione (GSH), interleukin-1 (IL-1), interleukin-3 (IL-3) and mast cell growth factor (MGF).

Growth of CFU-GM, BFU-E and CFU-GEMM colonies from marrow mononuclear cells was determined using a modification of techniques previously described (Pike and Robinson, 1970, J. Cell. Physiol. 76: 77–84). Following drug exposure, 1 ml suspensions of mononuclear cells in Iscove Modified Dulbecco Medium, 0.8% methylcellulose, 30% fetal calf serum, erythropoietin, and 5% phytohemagglutinin-stimulated leukocyte-conditioned media (PHA-LCM) or fetal calf serum were plated in triplicate in 35 ml Petri dishes and incubated in a humidified atmosphere with 5% $CO_2$, at 37° C. Granulocyte/macrophage colonies (CFU-GM) containing 40 cells and clusters (3–40 cells) were scored after 7 days using an inverted microscope and results expressed as mean colony number per $2\times10^6$ cells plated. BFU-E and CFU-GEMM were scored after 14 days incubation. Mean colony number was compared in the presence or absence of amifostine or WR-1065 and expressed as a percent of control.

6.2. Results

WR2721 and WR1065 (3 mg/ml) increased CFU-GEMM and BFU-E recovery in normal marrow up to 7-fold (median, 3-fold), whereas minor stimulation of CFU-GM was observed (range: 1.5-to 3-fold). Dose-dependent stimulation of progenitor cell growth occurred with each thiol over a concentration of 0.1–1000 μM; although GSH was cytotoxic at higher concentrations. Extending thiol exposure up to 24 hr. yielded no further enhancement of progenitor recovery. Compared with MGF, IL-1, and IL-3 (100 U/ml), pre-incubation with WR2721 (10 μM) or WR1065 (1.0 μM) at low physiologic concentrations yielded up to 3-fold greater recovery of BFU-E and CFU-GEMM. These findings indicate that WR2721 and WR1065 are potent stimulants of hematopoietic progenitor cell growth, exceeding in potency the recombinant cytokines tested.

Results from treatment of bone marrow from four patients with MDS are noted in FIGS. 1A to 1D. Marrow suspensions were exposed to either 100 or 500 μM amifostine and then plated. Stimulation of marrow progenitor growth was as follows: CFU-GEMM colony growth was increased by approximately 225% of control in 2 of 4 patients; BFU-E colony growth was increased by 300–650% of control in 3 of 4 patients; CFU-GM was increased by 150–350% of control in 2 of 4 patients. Thus, the thiols disclosed herein stimulate hematopoietic cell growth in both normal and diseased bone marrow.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method of stimulating hematopoietic progenitor cells, which comprises:

exposing hematopoietic progenitor cells to an effective amount of a compound selected from the group consisting of S-2-(3-aminopropylamino)ethyl dihydrogen phosphorothioate (WR 2721), 1-propanethiol-3-[[3-(methylamino)propyl]amino]-dihydrogen phosphorothioate (WR 151327), 2-[(3-aminopropyl)amino]-ethanethiol (WR 1065), and 3-[[3-(methylamino)propyl]amino]-1-propanethiol (WR 151326), or a pharmaceutically acceptable salt, hydrate or solvate thereof; and stimulating the hematopoietic progenitor cells to develop into blood cells.

2. The method of claim 1, wherein the pharmaceutically acceptable salt is an alkali metal salt or a halogen salt.

3. The method of claim 1, wherein the compound is S-2-(3-aminopropylamino)ethyl dihydrogen phosphorothioate (WR 2721) or a pharmaceutically acceptable salt, hydrate or solvate thereof.

4. The method of claim 1, wherein the compound is 1-propanethiol-3-[[3-(methylamino)propyl]amino]-dihydrogen phosphorothioate (WR 151327) or a pharmaceutically acceptable salt, hydrate or solvate thereof.

5. The method of claim 1, wherein the compound is 2-[(3-aminopropyl)amino]-ethanethiol (WR 1065) or a pharmaceutically acceptable salt, hydrate or solvate thereof.

6. The method of claim 1, wherein the compound is 3-[[3-(methylamino)propyl]amino]-1-propanethiol (WR 151326) or a pharmaceutically acceptable salt, hydrate or solvate thereof.

7. A method of stimulating hematopoietic progenitor cells in a subject, which comprises:

administering to a subject in need thereof a therapeutically effective amount of a compound selected from the group consisting of S-2-(3-aminopropylamino)ethyl dihydrogen phosphorothioate (WR 2721), 1-propanethiol-3-[[3-(methylamino)propyl]amino]-dihydrogen phosphorothioate (WR 151327), 2-[(3-aminopropyl)amino]-ethanethiol (WR 1065), and 3-[[3-(methylamino)propyl]amino]-1-propanethiol (WR 151326), or a pharmaceutically acceptable salt, hydrate or solvate thereof; and stimulating an increased number of blood cells in the subject.

8. The method of claim 7, wherein the pharmaceutically acceptable salt is an alkali metal salt or a halogen salt.

9. The method of claim 7, wherein said subject is a human.

10. The method of claim 7, wherein the compound is S-2-(3-aminopropylamino)ethyl dihydrogen phosphorothioate (WR 2721) or a pharmaceutically acceptable salt, hydrate or solvate thereof.

11. The method of claim 7, wherein the compound is 1-propanethiol-3-[[3-(methylamino)propyl]amino]-dihydrogen phosphorothioate (WR 151327) or a pharmaceutically acceptable salt, hydrate or solvate thereof.

12. The method of claim 7, wherein the compound is 2-[(3-aminopropyl)amino]-ethanethiol (WR 1065) or a pharmaceutically acceptable salt, hydrate or solvate thereof.

13. The method of claim 7, wherein the compound is 3-[[3-(methylamino)propyl]amino]-1-propanethiol (WR 151326) or a pharmaceutically acceptable salt, hydrate or solvate thereof.

14. A method of treating marrow failure state in a subject, which comprises:

administering to a subject suffering from marrow failure state a therapeutically effective amount of a compound selected from the group consisting of S-2-(3-aminopropylamino)ethyl dihydrogen phosphorothioate (WR 2721), 1-propanethiol-3-[[3-(methylamino) propyl]amino]-dihydrogen phosphorothioate (WR 151327), 2-[(3-aminopropyl)amino]-ethanethiol (WR 1065), and 3-[[3-(methylamino)propyl]amino]-1-propanethiol (WR 151326), or a pharmaceutically acceptable salt, hydrate or solvate thereof; and stimulating an increased number of blood cells in the subject.

15. The method of claim 14, wherein the pharmaceutically acceptable salt is an alkali metal salt or a halogen salt.

16. The method of claim 14, wherein said subject is a human.

17. The method of claim 14, wherein the compound is S-2-(3-aminopropylamino)ethyl dihydrogen phosphorothioate (WR 2721) or a pharmaceutically acceptable salt, hydrate or solvate thereof.

18. The method of claim 14, wherein the compound is 1-propanethiol-3-[[3-(methylamino)propyl]amino]-dihydrogen phosphorothioate (WR 151327) or a pharmaceutically acceptable salt, hydrate or solvate thereof.

19. The method of claim 14, wherein the compound is 2-[(3-aminopropyl)amino]-ethanethiol (WR 1065) or a pharmaceutically acceptable salt, hydrate or solvate thereof.

20. The method of claim 14, wherein the compound is 3-[[3-(methylamino)propyl]amino]-1-propanethiol (WR 151326) or a pharmaceutically acceptable salt, hydrate or solvate thereof.

21. The method of claim 14, wherein the marrow failure state is Fanconi anemia, congenital neutropenia or myelodysplastic syndrome.

22. The method of claim 21, wherein the marrow failure state is myelodysplastic syndrome.

* * * * *